United States Patent
Zhao et al.

(10) Patent No.: US 11,858,970 B1
(45) Date of Patent: Jan. 2, 2024

(54) CHILI PEPPER SEED ISOLATED OLIGOPEPTIDE FTLE AND APPLICATION THEREOF IN PREVENTING OR TREATING CANCER

(71) Applicant: CHINA AGRICULTURAL UNIVERSITY, Beijing (CN)

(72) Inventors: Liang Zhao, Beijing (CN); Xiaojun Liao, Beijing (CN); Fengzhang Wang, Beijing (CN); Yongtao Wang, Beijing (CN); Lei Rao, Beijing (CN)

(73) Assignee: CHINA AGRICULTURAL UNIVERSITY, Beijing (CN)

( * ) Notice: Subject to any disclaimer, the term of this patent is extended or adjusted under 35 U.S.C. 154(b) by 0 days.

(21) Appl. No.: 18/169,149

(22) Filed: Feb. 14, 2023

(30) Foreign Application Priority Data

Jun. 29, 2022 (CN) .......................... 202210744912.4

(51) Int. Cl.
| | | |
|---|---|---|
| *C07K 9/00* | (2006.01) | |
| *C07K 14/415* | (2006.01) | |
| *C07K 1/14* | (2006.01) | |
| *A61K 38/00* | (2006.01) | |

(52) U.S. Cl.
CPC ............ *C07K 14/415* (2013.01); *C07K 1/145* (2013.01); *A61K 38/00* (2013.01)

(58) Field of Classification Search
CPC ....... C07K 14/415; C07K 1/145; A61K 38/00
See application file for complete search history.

(56) References Cited

U.S. PATENT DOCUMENTS

| | | |
|---|---|---|
| 2006/0239968 A1 | 10/2006 | Arap et al. |
| 2010/0120685 A1 | 5/2010 | Bu |
| 2012/0308590 A1 | 12/2012 | Nishimura et al. |

FOREIGN PATENT DOCUMENTS

| | | |
|---|---|---|
| CN | 105132506 A | 12/2015 |
| CN | 112111003 A | 12/2020 |
| CN | 113784974 A | 12/2021 |
| WO | 2021234165 A1 | 11/2021 |

OTHER PUBLICATIONS

Bley et al. Toxicologic Pathology, 40: 847-873, 2012.*
National Institute of Cancer—understanding and related topics, accessed Jun. 16, 23, at URL: https://www.cancer.gov/about-cancer/understanding/what-is-cancer.*
First Office Action from corresponding Chinese Application No. 202210744912.4, dated Aug. 12, 2022. English translation attached.
The Grant Notice from corresponding Chinese Application No. 202210744912.4, dated Aug. 19, 2022. English translation attached.
Xiao HU et al. "Preparation and Purification of Antioxidant Peptide from Porphyra haitanensis Protein and Its Antioxidant Activities in Vitro" Food Science, 2020, vol. 41(16): 37-44, Aug. 2020 (Aug. 2020).
Lanlan Zheng et al. "Research Progress of Plant Antimicrobial Peptides with Antitumor Activity" Worldnotes on Antibiotics, 2017, vol. 38(6): 279-283, Nov. 2017 (Nov. 2017).
Peixin Wang et al. "The research progress of anti-fatigue peptides" Journal of Fujian Agriculture and Forestry University ( Natural Science Edition), 2019, vol. 48(3), May 2019 (May 2019).

* cited by examiner

*Primary Examiner* — Jeanette M Lieb

(57) ABSTRACT

The present disclosure provides an oligopeptide FTLE isolated from chili pepper seeds, and application thereof in preventing or treating cancer, the oligopeptide is isolated from chili pepper seeds and has an anti-tumor effect, and in particular, the oligopeptide can effectively inhibit the growth and metabolism of HepG2 cells, and has a good application prospect.

5 Claims, 1 Drawing Sheet
Specification includes a Sequence Listing.

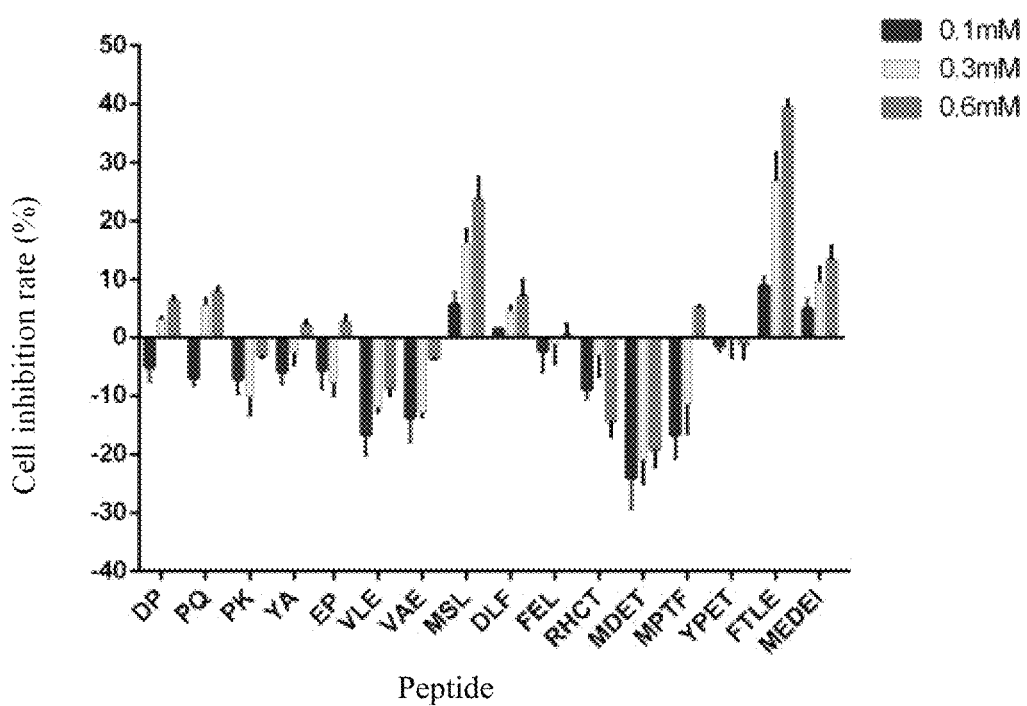

CHILI PEPPER SEED ISOLATED OLIGOPEPTIDE FTLE AND APPLICATION THEREOF IN PREVENTING OR TREATING CANCER

CROSS-REFERENCE TO RELATED APPLICATIONS

This application claims priority to Chinese Patent Application NO. 202210744912.4, filed on Jun. 29, 2022, the entire disclosure of which is incorporated here by reference.

TECHNICAL FIELD

The present disclosure relates to the biological field. In particular, the present disclosure relates to a chili pepper seed isolated oligopeptide FTLE and the application thereof in preventing or treating cancer.

BACKGROUND

Chili pepper, an herb of the genus chili pepper of Solanaceae, is originated in Mexico and later spread to China. Chili peppers are now mainly planted in provinces Sichuan, Yunnan, Guizhou, Hunan, Henan, and other places of China. The chili pepper is mainly composed of chili pepper flesh and chili pepper seeds. The chili pepper seeds account for 30% to 60% of the dry weight of the chili pepper and are the main by-product in the processing of chili pepper. Chili pepper seeds are rich in dietary fiber, fat, protein, minerals, and vitamin E, and have excellent nutritional and economic value.

With the rapid development of chili pepper processing industry in China, chili pepper has been applied in food, medicine, the chemical industry, and other fields. In the field of food, there are more and more chili pepper products, such as dried chili, chili sauce, chili powder, hot pot primer, etc. Chili pepper is also widely used in medicine. A large quantity of discarded chili pepper seeds will be produced during chili pepper processing. At present, a small part of chili pepper seeds in China are used as animal feed, but most of them are treated as waste without effective use, which causes environmental pollution and waste of resources. Chili pepper seeds are high-quality protein resources because of the high yield, low price, easy access, complete amino acids in cake protein, and moderate content of essential amino acids. Therefore, extraction of bioactive peptides from chili pepper seeds can not only change waste into treasure, and improve the utilization of resources, but also reduce pollution, in line with the development goals of an environmental-friendly society.

Currently, anti-tumor drugs such as fluorouracil, cisplatin, daunorubicin, etc. play an important role in tumor treatment, but the clinical applicability of these drugs is limited due to their safety performance, effectiveness, and high price. More and more studies have shown that bioactive peptides from natural foods or animals and plants have a positive effect on human health. The physiological functions of bioactive peptides are mainly embodied in antibacterial, antiviral, antioxidant, antitumor, hypoglycemic, hypotensive, cholesterol-lowering, immunomodulatory, and other aspects. Animal-derived bioactive peptides have problems of high cost and safety, while plant-derived bioactive peptides, such as soybean bioactive peptides, peanut bioactive peptides, and rapeseed bioactive peptides, have been widely used for their natural and high nutritional value. However, research on bioactive peptides from chili pepper seeds is still scarce.

SUMMARY

The present disclosure aims to solve, at least to some extent, at least one of the technical problems existing in the related art.

In one aspect of the present disclosure, the present disclosure provides an isolated polypeptide. According to an embodiment of the present disclosure, the isolated oligopeptide has an amino acid sequence set forth in SEQ ID NO: 1 or a functional analog thereof. In particular, the amino acid sequence of the isolated oligopeptide is FTLE (Phe-Thr-Leu-Glu, SEQ ID NO: 1). The inventor isolated the oligopeptide described above from the chili pepper seeds, studied the functions, and found that the oligopeptide has an anti-tumor effect, and especially can effectively inhibit the growth and metabolism of HepG2 cells, with a good application prospect.

According to an embodiment of the present disclosure, the isolated oligopeptide is derived from chili pepper seeds. The inventor extracted the protein from the chili pepper seeds and surprisingly found the above oligopeptide with the anti-tumor effect.

In another aspect of the present disclosure, provided is a nucleic acid molecule. According to an embodiment of the present disclosure, the nucleic acid molecule encodes the isolated oligopeptide as described above. The nucleic acid molecule according to an embodiment of the present disclosure, upon being introduced into a recipient cell, can express the above-described isolated oligopeptide with the anti-tumor effect in an environment suitable for protein expression.

It should be noted that the sequence of the nucleic acid molecule of the present disclosure is not strictly limited as long as it is capable of encoding the isolated oligopeptide described above. In another aspect of the present disclosure, provided is a construct. According to an embodiment of the present disclosure, the construct includes the nucleic acid molecule described above. The construct according to an embodiment of the present disclosure, upon being introduced into a cell, can express the isolated oligopeptide described above in an environment suitable for protein expression, which is helpful to exert the anti-tumor effect of the oligopeptide.

In yet another aspect of the present disclosure, provided is a recombinant cell. According to an embodiment of the present disclosure, the recombinant cell includes the nucleic acid molecule described above or the construct described above. Thus, the recombinant cell can express the isolated oligopeptide described above in an environment suitable for protein expression, which is helpful to exert the anti-tumor effect of the oligopeptide. The recombinant cells of the present disclosure do not include germ cells, fertilized egg cells, or embryonic cells.

In yet another aspect of the present disclosure, provided is medicament or food. According to an embodiment of the present disclosure, the medicament or food includes an isolated oligopeptide, nucleic acid molecule, or recombinant cell described above. Thus, the medicament or food according to the embodiment of the present disclosure has an effect of preventing or treating cancer.

In a further aspect of the present disclosure, provided is the use of the oligopeptide, nucleic acid molecule, or recombinant cell as described above for the preparation of a medicament or food. According to an embodiment of the present disclosure, the medicament or food is used for preventing or treating cancer.

According to an embodiment of the present disclosure, the cancer is breast cancer, lung cancer, nasopharyngeal cancer, liver cancer, gastric cancer, esophageal cancer, colorectal cancer, pancreatic cancer, melanoma, skin cancer, prostate cancer, cervical cancer, leukemia, thyroid cancer, lymphoma, bladder cancer, renal cancer, endometrial carcinoma, ovarian cancer, gallbladder cancer, oral cancer, laryngocarcinoma, bone cancer, testicular cancer, or brain cancer.

In yet another aspect of the present disclosure, provided is a method for obtaining the isolated oligopeptide described above. According to an embodiment of the present disclosure, the method includes treating chili pepper seeds to obtain the isolated oligopeptide. According to an embodiment of the present disclosure, the method includes: step 1 of pulverizing the chili pepper seeds to obtain chili pepper seed powder; step 2 of degreasing the chili pepper seed powder to obtain a degreased chili pepper seed meal; step 3 of extracting protein from the degreased chili pepper seed meal to obtain a crude protein extract; step 4 of performing an enzymolysis treatment on the crude protein extract followed by enzyme inactivation to obtain an enzymolytic protein solution; and step 5 of isolating and purifying the enzymolytic protein solution to obtain the isolated oligopeptide.

In step 1, by pulverizing the chili pepper seeds, the subsequent reaction can be performed better and the reaction can be more sufficient, thereby improving the yield and purity of oligopeptide. In step 2, the degreasing treatment can remove the oil and fat from the chili pepper seed powder, thereby improving the extraction rate and purity of the protein. In step 4, by the enzymolysis treatment, the protein can be enzymatically hydrolyzed into small-molecule peptides effectively, which is helpful to obtain the oligopeptide with the anticancer function.

According to an embodiment of the present disclosure, in step 1, the pulverized material obtained by the pulverizing is sieved by a 60 to 100 mesh sieve to obtain a retentate and an undersize material, and the undersize material is collected to obtain the chili pepper seed powder. In this way, the chili pepper seed powder can pass through the sieve and the impurities can be retained, thereby improving the protein extraction rate, and avoiding the influence of impurities.

According to an embodiment of the present disclosure, a degreasing solvent used in the degreasing is n-hexane. Thus, the fat can be effectively removed, which is safe to use.

According to an embodiment of the present disclosure, step 3 includes mixing the degreased chili pepper seed meal with water, adjusting a pH value of the resulting mixture to 9 to 10 with an alkaline solution, reacting for 3 to 5 hours, then adjusting a pH value of the reaction solution to 4 to 5, reacting for 1 to 3 hours, centrifuging the reaction solution, and collecting the precipitate to obtain the crude protein extract. The higer pH value is used first so that the protein in the chili pepper seed meal can be dissolved in an alkaline environment. Then, the pH value is lowered so that the protein can be precipitated at the isoelectric point of the protein. The isolated protein can be obtained after centrifugation.

According to an embodiment of the present disclosure, the crude protein extract is subjected to an ultra-high pressure treatment in advance before the enzymolysis treatment in step 4. The ultra-high pressure treatment can improve the physical and chemical properties of the protein. The activity of the product obtained by ultra-high pressure treatment and enzymolysis is higher than that obtained by enzymolysis alone.

According to an embodiment of the present disclosure, the ultra-high pressure treatment is performed at a pressure of 100 to 400 MPa for 20 to 40 min. Thus, it helps to improve the physical and chemical properties of protein and enhance the activity of the product obtained by enzymolysis.

According to an embodiment of the present disclosure, the enzymolysis treatment is performed at a temperature of 30to 50° C. under a pH value of 7 to 10 for 1 to 5 hours. The enzyme used in the enzymolysis treatment is selected from alkaline proteases, preferably *Bacillus licheniformis*, and a mass ratio of the enzyme to the crude protein extract ranges from 1:20 to 1:50. Thus, the protein is enzymatically hydrolyzed into small peptides to obtain the anticancer oligopeptide.

According to an embodiment of the present disclosure, the enzyme inactivation is performed at 90 to 100° C. for 1 to 10 min. Thus, the enzyme is inactivated to prevent overreaction or to prevent the enzyme from interfering with subsequent experiments.

According to an embodiment of the present disclosure, in step 5, the isolating and purifying are performed using chromatography columns, and the chromatographic columns include an anion chromatographic column and a hydrophobic chromatographic column. A mobile phase used for the anion chromatography columnincludes water and NaCl; and a mobile phase used for the hydrophobic chromatographic column includes water and a 40 to 60 v/v% methanol solution.

According to an embodiment of the present disclosure, in step 5, the isolating and purifying include: injecting the enzymolytic protein solution into the anion chromatography column, eluting with the mobile phase, and collecting the effluent in a period from 35 min to min; and injecting the effluent into the hydrophobic chromatography column, eluting with the mobile phase, and collecting the effluent in a period from 75 min to 90 min to obtain a purified product containing the oligopeptide.

The inventor obtained the preferable isolation and purification method described above through a large number of experiments, and thus obtained the isolated oligopeptide described above.

Additional aspects and advantages of the present disclosure will be given in part in the following description, and in part will become apparent from the following description, or learned from the practice of the present disclosure.

BRIEF DESCRIPTION OF DRAWINGS

The foregoing and/or additional aspects and advantages of the present disclosure will become apparent and readily appreciated from the following description of the embodiments taken in conjunction with the accompanying drawings, in which:

Figure shows a schematic representation of an analysis of the effect of different peptide fragments on HepG2 cell proliferation according to an embodiment of the present disclosure.

DESCRIPTION OF EMBODIMENTS

Solutions of the present disclosure will be explained below in connection with examples. Those skilled in the art will appreciate that the following examples are only illustrative of the present disclosure and are not to be construed as limiting the scope of the present disclosure. If no specific technology or conditions are indicated in the embodiments, the technology or conditions described in the literature in this field or the product specification shall be followed. The reagents or instruments used of which the manufacturer is not noted are conventional products commercially available.

Example 1

In this example, the oligopeptide FTLE in chili pepper seeds was extracted as follows:

1) deseeding: fresh chili peppers were taken, and the flesh was separated from the seeds to obtain chili pepper seeds;

2) pulverizing: the chili pepper seeds were pulverized and sieved by an 80 mesh to obtain chili pepper seed powder;

3) degreasing: the chili pepper seed powder was mixed with n-hexane at a ratio of 1:10 (g/ml); the mixture was stirred and degreased overnight; n-hexane was removed by suction filtration after the degreasing was completed to obtain a chili pepper seed meal;

4) protein extraction: the degreased chili pepper seed meal was dissolved in water at a ratio of 1:10 (w/v, g/mL); the pH value of the solution was adjusted to 9.5 with a NaOH solution to conduct dissolving for 4 h; then the pH value of the solution was adjusted to 4.5 with HCl to conduct precipitating for 2 h; the reaction solution was centrifuged at 8,000 rpm for 20 min, and the precipitate was collected as a crude protein extract;

5) ultra-high pressure assisted enzymolysis: the protein isolated was dissolved in water, and was subjected to an ultra-high pressure treatment at 300 MPa for 30 min; then the product obtained by the ultra-high pressure treatment was subjected to an enzymolysis treatment, in which the enzyme was Bacillus licheniformis, the mass ratio of the enzyme to the substrate was 1:20 (w/w, g/g), the temperature was 40° C., the pH value was adjusted to 8 with 1 mol/L NaOH, and the enzymolysis treatment was performed for 3 h;

6) enzyme inactivation: at the end of the enzymolysis, the enzyme was inactivated at 90° C. for 10 min to obtain a chili pepper seed zymolyte solution;

7) isolation and purification of zymolyte: the chili pepper seed zymolyte solution was passed through a DEAE anion chromatography column, where the mobile phase included deionized water and NaCl; the eluent in a period from 35 min to 45 min was collected; then, isolation and purification were conducted by an ODS-A reverse phase C18 column (hydrophobic column), where the mobile phase included deionized water and 50% methanol, and the eluent in a period from 75 min to 90 min was collected. The peptide fragments in the obtained eluate were subjected to mass spectrometry identification analysis, and information of multiple peptide sequences was obtained.

Example 2

Chemical systhesis was conducted in accordance with the peptide sequences obtained by mass spectrometry identification analysis of Example 1 to obtain synthetic peptides. The effect of each peptide on HepG2 cell proliferation was studied, and the specific steps were as follows:

1) HepG2 cell culture: hepG2 cells were obtained from the ATCC cell bank and were cultured in a DMEM medium containing 10% FBS at 37° C. in a 5% $CO_2$ cell incubator. Cells were cultured in a 25 $cm^2$ flask, passaged when cells were grown to a density of 70% to 90%, and seeded in a 96-well plate.

2) Peptide fragment treatment: after 24 hours of cell culture in the 96-well plate, the original DMEM medium was aspirated from the wells. DMEM containing peptide fragments at concentrations of 0.1, 0.3, and 0.6 mM were added to each well to continue culturing for 24 hours.

3) Cell proliferation rate measured by MTT method: MTT at a concentration of 5 mg/mL was added to a 96-well plate in 20 μL per well. After incubation for 4 hours, the liquid was aspirated from each well. 150 μL DMSO was added to each well. The absorbance was measured after reacting for 20 min.

The results are shown in the figure. It can be seen that the oligopeptide FTLE has a better HepG2 cell inhibition rate than other oligopeptides, which is helpful for the prevention or treatment of liver cancer.

In the description of this specification, descriptions with reference to the terms "one embodiment", "some embodiments", "example", "specific examples", or "some examples", etc. mean that a particular feature, structure, material, or characteristic described in connection with the embodiment or example is included in at least one embodiment or example of the present disclosure. In this description, schematic representations of the terms above do not necessarily refer to the same embodiment or example. Furthermore, the particular features, structures, materials, or characteristics described may be combined in any suitable manner in any one or more embodiments or examples. The different embodiments or examples and the features of the different embodiments or examples described in this description can be integrated and combined by a person skilled in the art without contradicting each other.

While embodiments of the present disclosure have been shown and described, it will be understood that the above-described embodiments are illustrative and not restrictive and that changes, modifications, substitutions, and variations may be made to the embodiments by those skilled in the art without departing from the scope of the present disclosure.

SEQUENCE LISTING

```
Sequence total quantity: 1
SEQ ID NO: 1          moltype = AA  length = 4
FEATURE               Location/Qualifiers
source                1..4
                      mol_type = protein
                      organism = synthetic construct
SEQUENCE: 1
FTLE                                                                  4
```

What is claimed is:

1. A method for treating liver cancer, comprising: administrating an isolated oligopeptide consisting of an amino acid sequence set forth in SEQ ID NO: 1 to a subject in need thereof.

2. A method for obtaining an isolated oligopeptide consisting of an amino acid sequence set forth in SEQ ID NO: 1, comprising:
   treating chili pepper seeds to obtain the isolated oligopeptide.

3. The method according to claim 2, comprising:
   step 1 of pulverizing the chili pepper seeds to obtain chili pepper seed powder;
   step 2 of degreasing the chili pepper seed powder to obtain a degreased chili pepper seed meal;
   step 3 of extracting protein from the degreased chili pepper seed meal to obtain a crude protein extract;
   step 4 of performing an enzymolysis treatment on the crude protein extract, followed by enzyme inactivation, to obtain an enzymolytic protein solution; and
   step 5 of isolating and purifying the enzymolytic protein solution to obtain the isolated oligopeptide.

4. The method according to claim 3, wherein in step 1, the pulverized material obtained by the pulverizing is sieved by a 60 to 100 mesh sieve to obtain a retentate and an undersize material, and the undersize material is collected to obtain the chili pepper seed powder;
   in step 2, a degreasing solvent used in the degreasing is n-hexane;
   step 3 comprises: mixing the degreased chili pepper seed meal with water, adjusting a pH value of the resulting mixture to 9 to 10 with an alkaline solution, reacting for 3 to 5 hours, then adjusting a pH value of the reaction solution to 4 to 5, reacting for 1 to 3 hours, centrifuging the reaction solution, and collecting the precipitate to obtain the crude protein extract;
   the crude protein extract is subjected to an ultra-high pressure treatment in advance before the enzymolysis treatment in step 4, wherein the ultra-high pressure treatment is performed at a pressure of 100 to 400 MPa for 20 to 40 min;
   the enzymolysis treatment is performed at a temperature of 30 to 50° C. under a pH value of 7 to 10 for 1 to 5 hours;
   the enzyme used in the enzymolysis treatment is selected from alkaline proteases, and a mass ratio of the enzyme to the crude protein extract ranges from 1:20 to 1:50;
   the enzyme inactivation is performed at 90 to 100° C. for 1 to 10 min; and
   in step 5, the isolating and purifying are performed using chromatographic columns, wherein the chromatographic columns comprise an anion chromatographic column and a hydrophobic chromatographic column, wherein a mobile phase used for the anion chromatography column comprises water and NaCl, and a mobile phase used for the hydrophobic chromatographic column comprises water and a 40 to 60 v/v% methanol solution.

5. The method according to claim 4, wherein the enzyme used for the enzymolysis treatment is selected from Bacillus licheniformis; and
   in step 5, the isolating and purifying comprise:
   injecting the enzymolytic protein solution into the anion chromatography column, eluting with the mobile phase, and collecting the effluent in a period from 35 min to 45 min; and
   injecting the effluent into the hydrophobic chromatography column, eluting with the mobile phase, and collecting the effluent in a period from 75 min to 90 min to obtain a purified product containing the oligopeptide.

* * * * *